United States Patent
Jo et al.

(10) Patent No.: US 10,043,965 B2
(45) Date of Patent: Aug. 7, 2018

(54) ULTRASONIC WAVE CONVERTER, ELECTRIC PULSE GENERATING DEVICE, AND ULTRASONIC WAVE GENERATING DEVICE COMPRISING SAME

(71) Applicant: So-Yuon Jo, Changwon-si, Gyeongsangnam-do (KR)

(72) Inventors: So-Yuon Jo, Changwon-si (KR); Sung-Chan Jo, Seongnam-si (KR); Hak-Seong Kang, Changwon-si (KR)

(73) Assignee: KORUST CO., LTD., Gyeonggi-Do (KR)

( * ) Notice: Subject to any disclaimer, the term of this patent is extended or adjusted under 35 U.S.C. 154(b) by 675 days.

(21) Appl. No.: 14/371,177

(22) PCT Filed: Nov. 8, 2012

(86) PCT No.: PCT/KR2012/009387
§ 371 (c)(1),
(2) Date: Jul. 8, 2014

(87) PCT Pub. No.: WO2013/105723
PCT Pub. Date: Jul. 18, 2013

(65) Prior Publication Data
US 2014/0354111 A1    Dec. 4, 2014

(30) Foreign Application Priority Data
Jan. 9, 2012 (KR) .................. 10-2012-0002368

(51) Int. Cl.
*H01L 41/09* (2006.01)
*H01L 41/04* (2006.01)
(Continued)

(52) U.S. Cl.
CPC .... *H01L 41/042* (2013.01); *A61B 17/320068* (2013.01); *A61B 90/98* (2016.02);
(Continued)

(58) Field of Classification Search
CPC ... B06B 1/0246; B06B 1/0253; B06B 1/0261; B06B 1/0215; H01L 41/042; H02N 2/14;
(Continued)

(56) References Cited

U.S. PATENT DOCUMENTS 4,653,000 A * 3/1987 Matsumoto ............. A61B 8/14
 600/443
5,095,890 A * 3/1992 Houghton ............. B06B 1/0253
 310/316.01
(Continued)

FOREIGN PATENT DOCUMENTS

GB 2414077 A 11/2005
JP S62-83588 U 5/1987
(Continued)

*Primary Examiner* — Thomas Dougherty
(74) *Attorney, Agent, or Firm* — Rabin & Berdo, P.C.

(57) ABSTRACT

An ultrasonic wave generating device includes: an ultrasonic transducer; and a variable pulse generating device which generates and outputs an electric pulse. The ultrasonic transducer comprises a piezoelectric element which receives electric pulse from the electric pulse generating device and vibrates, and a memory which stores characteristic information of the ultrasonic transducer. The electric pulse generating device includes a variable pulse generator which generates and outputs an electric pulse having at least one of a variable frequency, a variable voltage and a variable current, an information receiver which receives characteristic information of the ultrasonic transducer from the memory, and a controller controlling the variable pulse generator based on the characteristic information of the ultrasonic transducer received by the information receiver such that the variable pulse generator generates and outputs an electric pulse which has at least one of a variable frequency, a variable voltage and a variable current.

6 Claims, 2 Drawing Sheets

(51) Int. Cl.
  *A61B 17/32* (2006.01)
  *B06B 1/02* (2006.01)
  *A61B 90/98* (2016.01)
  *A61B 17/00* (2006.01)

(52) U.S. Cl.
  CPC .... *B06B 1/0215* (2013.01); *A61B 2017/0003* (2013.01); *A61B 2017/00154* (2013.01); *A61B 2017/00482* (2013.01); *B06B 2201/55* (2013.01)

(58) Field of Classification Search
  CPC ........ H02N 2/142; H02N 2/067; A61B 90/98; A61B 17/320068
  USPC .................................... 310/316.01, 315–319
  See application file for complete search history.

(56) References Cited

U.S. PATENT DOCUMENTS

| | | | |
|---|---|---|---|
| 8,308,721 B2* | 11/2012 | Shibata | A61B 17/32006 606/38 |
| 9,070,856 B1* | 6/2015 | Rose | H01L 41/042 |
| 2002/0089257 A1* | 7/2002 | Kato | H02N 2/142 310/316.02 |
| 2003/0107298 A1* | 6/2003 | Matsushita | H02N 2/142 310/316.02 |
| 2003/0199794 A1 | 10/2003 | Sakurai et al. | |
| 2004/0082857 A1* | 4/2004 | Schonenberger | A61B 8/4438 600/439 |
| 2007/0167881 A1 | 7/2007 | Takahashi | |
| 2007/0194660 A1* | 8/2007 | Hashimoto | G04C 3/12 310/316.01 |

FOREIGN PATENT DOCUMENTS

| | | |
|---|---|---|
| JP | H02-290281 A | 11/1990 |
| JP | H06-343200 A | 12/1994 |
| JP | H09-224386 A | 8/1997 |
| JP | 2002-209907 A | 7/2002 |
| JP | 2002-362723 A | 12/2002 |
| JP | 2003-170115 A | 6/2003 |
| JP | 2004-093271 A | 3/2004 |
| JP | 2009-115216 A | 5/2009 |
| JP | 2010-207607 A | 9/2010 |
| KR | 10-1995-0002062 B1 | 3/1995 |
| KR | 10-2001-0092867 A | 10/2001 |
| KR | 10-1065579 B1 | 9/2011 |

* cited by examiner

【FIG. 1】

ULTRASONIC WAVE CONVERTER, ELECTRIC PULSE GENERATING DEVICE, AND ULTRASONIC WAVE GENERATING DEVICE COMPRISING SAME

TECHNICAL FIELD

The present invention relates to an ultrasonic wave converter (i.e., ultrasonic transducer), an electric pulse generating device generating electric pulse, and an ultrasonic wave generating device including the same.

BACKGROUND ART

An ultrasonic transducer may be formed by making a piezoelectric resonant by forming electrodes on both sides of a piezoelectric element or by coupling a case to a piezoelectric resonant. If an electric pulse is applied to the electrodes of the piezoelectric resonant, the piezoelectric element resonates to generate ultrasonic wave.

Electric characteristics of an ultrasonic transducer are generally determined depending on material, shape, thickness, etc., of a piezoelectric element, and may be altered by an outer case, thickness of an adhesive layer, an operating environment, or adhesive material. Electric characteristics of an ultrasonic transducer may include a resonance frequency, an antiresonance frequency, a phase, an impedance, or the like, and if an electric pulse having the same frequency with the resonance frequency is applied to an ultrasonic transducer, the greatest ultrasonic wave energy may be output. The reason why an ultrasonic transducer outputs the greatest ultrasonic wave energy at the resonance frequency is that an impedance of an ultrasonic transducer is lowest at the resonance frequency. However, even if an electric pulse is applied with the resonance frequency, the output of the ultrasonic transducer may not be at the maximum value depending on characteristics of an electric pulse generating device. The reason of this is that the impedances of the electric pulse generating device and an ultrasonic transducer are different from one another, and this is caused by the fact that the maximum electric power is transmitted when the impedances of an electric power supplier and a load. Accordingly, in order to obtain the maximum ultrasonic wave output in an ultrasonic transducer, impedances together with the resonance frequencies should be matched with one another. For this function, impedance matching circuits may be additionally provided to an ultrasonic transducer and an electric pulse generating device.

However, since the electric characteristics of an ultrasonic transducer are altered very sensitively depending on various parameters as described above compared to an electric pulse generating device, it is difficult to perform the impedance matching. In particular, in case that an ultrasonic transducer is frequently replaced due to various reasons such as a life span, a disorder, or the like while the same electrical pulse generating device is used, it is much more difficult.

Recently, while ultrasonic wave is variously used in medical devices such as an ultrasonic wave stimulator, a high intensity focused ultrasonic device, frequency and energy of an ultrasonic wave become greater, so many techniques for increasing and stabilizing the output of the ultrasonic wave energy are being developed.

Generally, in order to increase a resonance frequency and an output intensity of an ultrasonic transducer, electrical connections such as a resonance frequency and an impedance matching are important together with physical conditions such as suitable material and shape of a piezoelectric element. However, as stated above, it is very difficult to manufacture an ultrasonic transducer having uniform electrical characteristics such as a resonance frequency and an impedance. Furthermore, in case that a resonance frequency of an ultrasonic transducer is high, a structure thereof is complicated, or an output intensity of ultrasonic wave is high, it is much more difficult to make characteristics of an ultrasonic transducer uniform. Due to such difficulties in a manufacturing process, ultrasonic transduces which have manufactured to have the same characteristics may actually have different characteristics. These differences may exert a bad influence on reactivation and treatment effect of the device. Although electrical characteristics are adjusted by adding impedance matching circuits to respective ultrasonic transducers, time for adding an impedance matching circuit is needed and manufacturing cost is increased.

DETAILED DESCRIPTION OF THE INVENTION

Technical Problem

The present invention has been made in an effort to provide an ultrasonic transducer, an electric pulse generating device, and an ultrasonic wave generating device including the same which can solve the problem that the output of ultrasonic wave is not uniform or the output intensity of ultrasonic wave is decreased due to the ununiformity of an ultrasonic transducer which is caused by various causes occurring in the manufacturing process of an ultrasonic transducer.

Technical Solution

An exemplary ultrasonic transducer for generating an ultrasonic wave according to an embodiment of the present invention includes: a piezoelectric element which receives electric pulse from an electric pulse generating device and vibrates; and a memory which stores characteristic information of the ultrasonic transducer.

The characteristic information may include at least one of a resonance frequency, an impedance, an output intensity for respective frequencies, an output intensity for respective supplied electric powers, a maximum output frequency, a maximum output intensity, an operation time and an operation number which are previously measured.

The ultrasonic transducer may further include an impedance matching circuit which is connected to the piezoelectric element.

An exemplary electric pulse generating device according to an embodiment of the present invention includes: a variable pulse generator which generates and outputs an electric pulse having a variable frequency; an information receiver which receives characteristic information of an ultrasonic transducer which will be supplied with the electric pulse; and a controller controlling the variable pulse generator based on the characteristic information of the ultrasonic transducer received by the information receiver such that the variable pulse generator generates and outputs an electric pulse which has at least one of a variable frequency, a variable voltage and a variable current.

The characteristic information of the ultrasonic transducer may include a resonance frequency of the ultrasonic transducer which is previously measured, and wherein the controller controls the variable pulse generator such that the variable pulse generator generates and outputs an electric pulse having the same frequency with the resonance frequency of the ultrasonic transducer.

The characteristic information of the ultrasonic transducer may include an ultrasonic wave output energy of the piezoelectric element which is previously measured, and wherein the controller controls the variable pulse generator such that the variable pulse generator generates and outputs an electric pulse for an output time which is calculated based on the ultrasonic wave output energy and an output intensity which is selected by a user.

An exemplary ultrasonic wave generating device according to an embodiment of the present invention includes: an ultrasonic transducer; and a variable pulse generating device which generates and outputs an electric pulse. The ultrasonic transducer comprises a piezoelectric element which receives electric pulse from the electric pulse generating device and vibrates, and a memory which stores characteristic information of the ultrasonic transducer. The electric pulse generating device includes a variable pulse generator which generates and outputs an electric pulse having at least one of a variable frequency, a variable voltage and a variable current, an information receiver which receives characteristic information of the ultrasonic transducer from the memory, and a controller controlling the variable pulse generator based on the characteristic information of the ultrasonic transducer received by the information receiver such that the variable pulse generator generates and outputs an electric pulse which has at least one of a variable frequency, a variable voltage and a variable current.

The characteristic information of the ultrasonic transducer may include a resonance frequency of the ultrasonic transducer which is previously measured, and the controller may control the variable pulse generator such that the variable pulse generator generates and outputs an electric pulse having the same frequency with the resonance frequency of the ultrasonic transducer.

The characteristic information of the ultrasonic transducer may include an ultrasonic wave output energy of the piezoelectric element which is previously measured, and the controller may control the variable pulse generator such that the variable pulse generator generates and outputs an electric pulse for an output time which is calculated based on the ultrasonic wave output energy and an output intensity which is selected by a user.

The characteristic information of the ultrasonic transducer may include at least one of an intrinsic impedance of the piezoelectric element and operation time and operation number of the piezoelectric element, and wherein the controller controls the variable pulse generator based on the characteristic information of the ultrasonic transducer.

Advantageous Effects

According to the present invention, since the characteristic information of the ultrasonic transducer including a piezoelectric element is stored and it can be used as a basic data for generating an electric pulse, characteristics which may be generated in the manufacturing process of the ultrasonic transducer and an ultrasonic wave having a desired output can be generated.

Further, since the characteristic information of the ultrasonic transducer includes a frequency or an output intensity of an ultrasonic wave, the output intensity which is chosen by a user can be precisely made, and the electric pulse can be applied for a specific time for the irradiation of the desired ultrasonic wave energy. Such an effect of the present invention can be maximized in case that an ultrasonic transducer which is expendable part is continuously replaced to the same system.

DETAILED DESCRIPTION OF THE EMBODIMENTS

An ultrasonic transducer, an electric pulse generating device, and an ultrasonic wave generating device according to embodiments of the present invention will now be described hereinafter with reference to the accompanying drawings.

An ultrasonic wave converter, i.e., an ultrasonic transducer is a device for receiving electric pulse and generating ultrasonic wave, and an electric pulse generating device is a device for generating electric pulse for driving a piezoelectric element of the ultrasonic transducer, and an ultrasonic wave generating device is a device corresponding to a combination of an ultrasonic transducer and an electric pulse generating device. Since an ultrasonic wave generating device includes an ultrasonic transducer and an electric pulse generating device, explanations for an ultrasonic transducer and an electric pulse generating device according to embodiments of the present invention will not be separately made but will be explained together with the explanation of an ultrasonic wave generating device according to an embodiment of the present invention.

Figure 1:
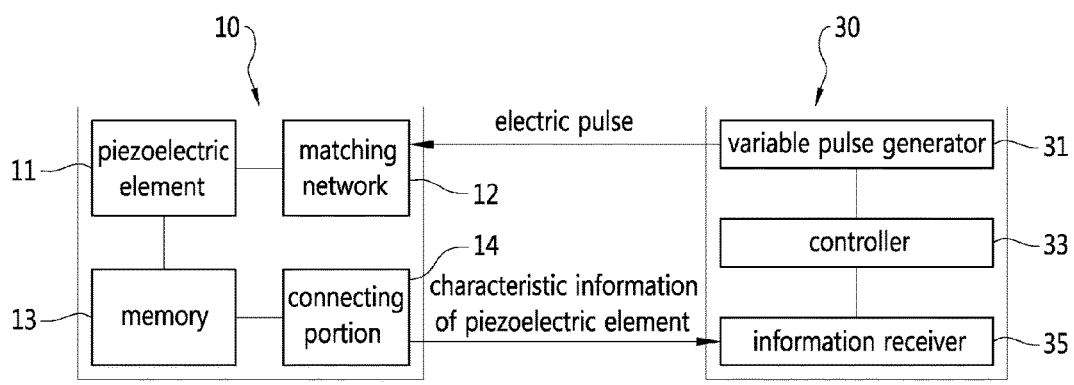
FIG. 1 is a block diagram of an ultrasonic wave generating device according to an embodiment of the present invention.

Referring to FIG. 1, an ultrasonic transducer 10 and an electric pulse generating device 30 are formed to be connectable to one another so as to send/receive electrical and information signals to/from one another. Since the ultrasonic transducer 10 generally has a shorter life span than the electric pulse generating device 30, the ultrasonic transducer 10 and the electric pulse generating device 30 may be formed as an independent unit, and may be connected to one another as needed. Accordingly, if the life of the ultrasonic transducer 10 expires, it may be replaced by a new ultrasonic transducer and the device can be reused.

The ultrasonic transducer 10 includes a piezoelectric element 11 which receives the electric pulse from the electric pulse generating device 30 and vibrates. The piezoelectric element 11 may be installed in a housing having a cage shape. For example, the piezoelectric element 11 may be formed by forming electrodes on both sides of a piezoceramic material layer, and if electrical signal is applied to the electrodes on both sides of the piezoceramic material layer, the piezoelectric element 11 vibrates.

Meanwhile, the ultrasonic transducer 10 may include a broad-band matching network 12 which is matched so as to receive electric pulse from the electric pulse generating device 30. For example, the matching network 12 may include an electric circuit which receives the electric pulse from the electric pulse generating device 30 and transmits the same to the piezoelectric element 11, and an impedance matching circuit for impedance matching between the electric pulse generating device 30 and the ultrasonic transducer 10.

Further, the ultrasonic transducer 10 may include a memory 13 which stores the whole characteristic information of the piezoelectric element 11 and the ultrasonic transducer 10. At this time, characteristic information may be obtained by connecting the ultrasonic transducer 10 to an electric pulse generating device which will be used and operating the same and by measuring characteristic information by measuring devices, or may be obtained from operation history information of the ultrasonic transducer 10, and may include various characteristic parameters of the ultrasonic transducer 10. For example, characteristic information may include a resonance frequency, an impedance, a phase, output intensities for respective frequencies, impedances for respective frequencies, output intensities for respective supplied electric voltage, maximum output frequency, maximum output intensity, operation time, operation number, and so on. For example, the maximum output frequency and the maximum output intensity may be obtained by measuring the frequency and the output intensity when the output intensity of output ultrasonic wave becomes maximum while an electric pulse having a specific frequency is applied. At this time, the characteristic information may be measured independently using a measuring device in a state of being realized as the ultrasonic transducer 10, and may also be measured in a state of being connected to a specific electric pulse generating device and being operated. For example, the maximum output frequency, the maximum output intensity, the output intensity for respective frequencies, and the like may be values which are measured in a state of being connected to a specific pulse generating device. At this time, the specific pulse generating device may be a device to which the manufactured ultrasonic transducer is used.

Further, a connecting portion 14 for connection with the electric pulse generating device 30 which will be explained later. The information which is stored in the memory 13 may be transmitted to the electric pulse generating device 30 via the connecting portion 14. For example, the connection portion 14 may be realized as a type of a terminal which can be connected to an information receiving portion 35 of the electric pulse generating device 30 which will be explained later. Meanwhile, the information stored in the memory 13 may be transmitted to the electric pulse generating device 30 via wireless communication such as Bluetooth communication.

Further, not shown in the drawing, the ultrasonic transducer 10 may further include an impedance matching circuit which is connected to the piezoelectric element 11. In case that characteristic values in a desired range of the ultrasonic transducer 10 is not obtained in the manufacturing process of the ultrasonic transducer 10, an impedance matching circuit which can regulate the impedance of the ultrasonic transducer 10 is provided, so processes for obtaining the desired ultrasonic wave output later becomes simple.

Meanwhile, the electric pulse generating device 30 includes a variable pulse generator 31. The variable pulse generator 31 is formed to generate electric pulse having variable frequencies and to output the same. That is, the variable pulse generator 31 may generate electric pulse having different frequencies in accordance with the required needs and may output the same. The electric pulse generating device having variable frequencies itself is obvious to a person skilled in the art, so further detailed explanation for the same will be omitted.

The electric pulse generated by the electric pulse generating device 30 is supplied to the ultrasonic transducer 10, and for this the electric pulse generating device 30 may include a cable through which the electric pulse is transmitted.

Figure 2:
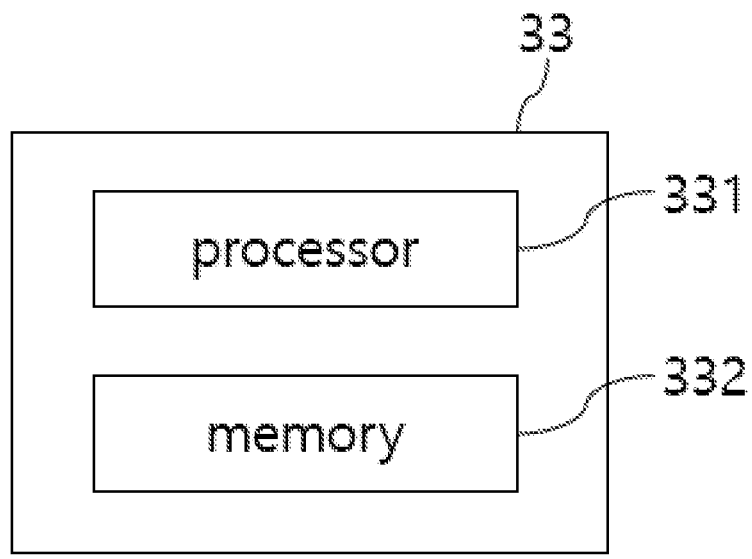
FIG. 2 illustrates main components of the controller 33 according to an embodiment of the present invention.

A controller 33 controls the variable pulse generator 31. For example, the controller 33 may control the variable pulse generator 31 to generate electric pulse having specific frequency, and may also control to generate and output electric pulse for a predetermined time. As shown in FIG. 2, the controller 33 may include a microprocessor 331, a memory 332, and other related hardware and software, and may be operated by a computer program which operates to perform a control method which will be explained later.

An information receiver 35 may receive the characteristic information of the ultrasonic transducer 10, which is supplied with the electric pulse, from the memory 13. For example, the information receiver 35 may be realized as an arbitrary device which receives information stored in the memory 13 of the ultrasonic transducer 10, and may be realized as an arbitrary device which can receive information from the connecting portion 14.

The characteristic information of the ultrasonic transducer 10 which has been received by the information receiver 35 is transmitted to the controller 33, and the controller 33 controls operation of the variable pulse generator 31 based on the transmitted characteristic information. That is, the controller 33 controls the variable pulse generator 31 based on the characteristic information of the ultrasonic transducer 10 such that the variable pulse generator 31 generates and outputs electric pulse in which at least one of the frequency and the voltage can be varied.

A detailed method by which the controller 31 controls the variable pulse generator 31 will be described hereinafter.

As an example, in case that the characteristic information of the ultrasonic transducer 10 includes the maximum output frequency of the corresponding ultrasonic transducer 10 which is previously measured, the controller 33 generates and outputs an electric pulse having the same frequency with the maximum output frequency of the ultrasonic transducer 10. Accordingly, the ultrasonic transducer 10 may be operated by an electric pulse having the same frequency of the maximum output frequency thereof which is previously measured, and thus the ultrasonic transducer 10 can output maximum ultrasonic wave energy.

Meanwhile, in case that the characteristic information of the ultrasonic transducer 10 includes the output energy of the corresponding ultrasonic transducer 10 which is previously measured, the controller 33 controls the variable pulse generator 31 such that the variable pulse generator 31 generates and outputs electric pulse for output time which is calculated based on the ultrasonic wave output intensity of the corresponding ultrasonic transducer 10 and the output energy which is selected by a user. The output energy which can be selected by a user can be determined by the following equation.

$$J = W*S,\qquad\text{[Equation]}$$

where J is the ultrasonic wave energy, W is the ultrasonic wave output intensity, and S is time.

For example, if the output intensity value of the ultrasonic transducer 10 and the output energy selected by a user are known, the output time can be obtained from the relation that the output energy is obtained by multiplying the output intensity value by the output time. At this time, the output intensity value can be set by the respective output intensity values stored in the memory 13 of the corresponding ultrasonic transducer 10 using the output intensity value corresponding to the frequency supplied by the electric pulse generating device. This method allows that the same ultrasonic wave output can be obtained using the characteristic information even though different ultrasonic transducers are connected to the same electric pulse generating device.

Furthermore, the characteristic information of the ultrasonic transducer 10 may further include at least one of operation time and operation number. In case that information of operation time and operation number are included to the characteristic information of the ultrasonic transducer 10, the controller 33 checks the operation time and the operation number of the corresponding ultrasonic transducer 10 and continuously updates and stores, so the history of operations of the corresponding ultrasonic transducer 10 can be easily managed.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

INDUSTRIAL APPLICABILITY

The present invention relates to an ultrasonic transducer, an electric pulse generating device and an ultrasonic wave generating device and can be applied to medical devices, so the present invention has an industrial applicability.

The invention claimed is:

1. An electric pulse generating device configured to be coupled with an ultrasonic transducer, comprising:
   a variable pulse generator configured to generate an electric pulse and to output the electric pulse to the ultrasonic transducer;
   an information receiver configured to receive characteristic information of the ultrasonic transducer, which is to be supplied with the electric pulse, from the ultrasonic transducer, the characteristic information including a resonance frequency of the ultrasonic transducer which is previously measured; and
   a controller including a processor and a memory having program instructions stored thereon, execution of which by the processor causes the controller
       to receive the characteristic information from the information receiver, and
       to control the variable pulse generator based on the received characteristic information, such that the electric pulse generated by the variable pulse generator has at least one of a variable frequency, a variable voltage, a variable output time and a variable current, wherein
   the electric pulse generated by the variable pulse generator has a same frequency as the resonance frequency of the ultrasonic transducer.

2. An ultrasonic wave generating device, comprising:
   an ultrasonic transducer; and
   the electric pulse generating device of claim 1,
   wherein the ultrasonic transducer includes
       a piezoelectric element which receives the electric pulse from the electric pulse generating device and vibrates, and
       another memory which stores the characteristic information of the ultrasonic transducer, and
   wherein the information receiver receives the characteristic information of the ultrasonic transducer from the another memory.

3. The electric pulse generating device of claim 1, wherein the characteristic information includes the resonance frequency of the ultrasonic transducer that is measured prior to start of operation of the ultrasonic transducer.

4. An electric pulse generating device configured to be coupled with an ultrasonic transducer, comprising:
   a variable pulse generator configured to generate an electric pulse and to output the electric pulse to the ultrasonic transducer;
   an information receiver configured to receive characteristic information of the ultrasonic transducer, which is to be supplied with the electric pulse, from the ultrasonic transducer; and
   a controller including a processor and a memory having program instructions stored thereon, execution of which by the processor causes the controller
       to receive the characteristic information from the information receiver, and
       to control the variable pulse generator based on the received characteristic information, such that the electric pulse generated by the variable pulse generator has at least one of a variable frequency, a variable voltage, a variable output time and a variable current,
   wherein the characteristic information of the ultrasonic transducer includes an ultrasonic wave output energy of the piezoelectric element which is previously measured, and
   wherein the controller controls the variable pulse generator such that the electric pulse generated by the variable pulse generator is for an output time calculated based on the ultrasonic wave output energy and a predetermined output intensity.

5. An ultrasonic wave generating device, comprising:
   an ultrasonic transducer; and
   the electric pulse generating device of claim 4,
   wherein the ultrasonic transducer includes
       a piezoelectric element which receives the electric pulse from the electric pulse generating device and vibrates, and
       another memory which stores the characteristic information of the ultrasonic transducer,
   wherein the information receiver receives the characteristic information of the ultrasonic transducer from the another memory.

6. The electric pulse generating device of claim 4, wherein the characteristic information includes the ultrasonic wave output energy of the piezoelectric element that is measured prior to start of operation of the ultrasonic transducer.

* * * * *